Oct. 15, 1974 J. C. MIKKELSEN Plant Pat. 3,638
BEGONIA PLANT
Filed Aug. 28, 1973
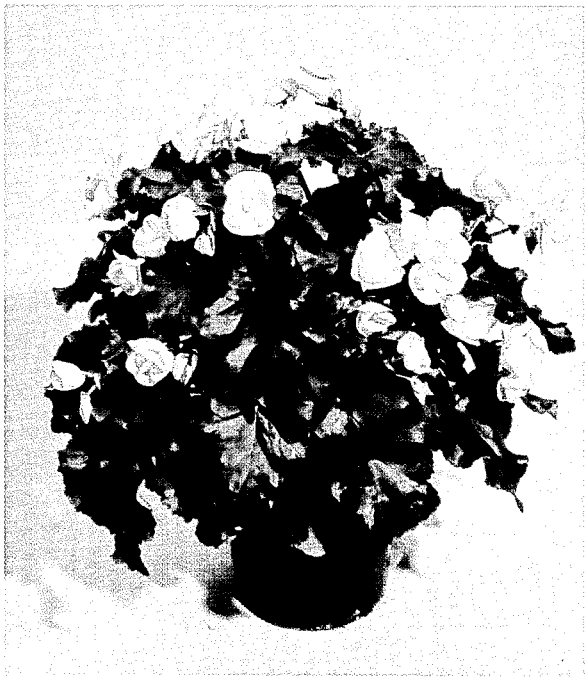

United States Patent Office

Plant Pat. 3,638
Patented Oct. 15, 1974

3,638
BEGONIA PLANT

James C. Mikkelsen, Ashtabula, Ohio, assignor to Mikkelsens, Inc, Ashtabula, Ohio Filed Aug. 28, 1973, Ser No. 392,359
Int Cl. A01h *5/00*
U.S. Cl. Plt.—68 1 Claim The present invention relates to a new and distinctive variety of begonia plant known botanically as *Begonia elatior* and known by the varietal name Improved Schwabenland Pink. The new cultivar was discovered by me as a mutation of the cultivar Riegers Schwabenland Pink.

The new mutation is distinguished from the parent variety by its flower color, leaf characteristics, and overall plant growth. The new cultivar was discovered as a flowering shoot in greenhouses in Ashtabula, Ohio, and has been asexually propagated by leaf cuttings through several succeeding generations, maintaining in all propagations its distinctive characteristics.

The important distinguishing features of the new variety when compared to the parent cultivar are:

1. The clear bluish pink coloring of the flower petals or bracts, having more bluish tones than the parent Riegers Schwabenland Pink, which has salmon pink petals.
2. Overall less floriferous.
3. Flowers being up to a centimeter larger.
4. A deeper green foliage which is also larger and heavier textured and which is susceptible to overall twisting as the leaves mature.
5. A more compact growth habit.

The following characteristics distinguish the new variety from other begonia cultivars of this general type:

1. Vigorous compact growth.
2. Generaly less floriferous with individual flower size being larger than related varieties. Individual flowers tend to be more distinctive when compared to other cultivars with greater masses of flowers.
3. Bright blue-pink petals that have uniform color retention throughout various environments of the year.
4. The quality of the blooms is maintained over a long period thereby providing exceptionally good keeping qualities for display purposes.
5. Flowers are almost exclusively masculine; single with generally four bracts; 6–7 centimeters in diameter, and carried on strong pedicels.
6. Propagation by leaf cuttings is very good with a high percentage producing multiple adventitious basal shoots.
7. Flower production timing is somewhat greater than Riegers Schwabenland Red or Pink.

The new cultivar is illustrated in the accompanying photographic drawing which is as true to color as it is reasonably possible to reproduce in a colored print of this type. The perspective view of the photograph clearly illustrates the above mentioned characteristics of flower color, foliage color and form, and overall plant form.

The following is a detailed description of my new begonia variety based on plants produced under commercial practices in Ashtabula, Ohio. As with most plant materials, the rate of growth, size of foliage, size and texture of flowers, and color intensity varies considerably with light and temperature conditions. The descriptions presented herewith are based on normal greenhouse practices unless otherwise noted. Color references are to the Royal Horticultural Society Colour Chart, except where general color terms of ordinary dictionary significance are used.

Parentage: A broad spectrum mutation from a previous mutant Riegers Schwabenland Pink which was in turn derived from the original hybrid Riegers Schwabenland Red.

Propagation: Continuous and successive vegetative propagation and subsequent flowering of plants developed from leaf cuttings indicates that the mutation is stable and reproduces true to type.

Rooting Habit: Rooting is average for this type of begonia propagated by leaf cuttings. Initiation and development of adventitious shoots is comparable to the other Rieger Schwabenland types.

Plant Form: Plants are compact, slightly dwarf, with considerable self branching and basal shooting.

Habit of Growth: Vigorous, upright, self branching, needing little if any support when well grown. Can be efficiently grown in all areas throughout the year.

Blooming Habits: Flowers are consistently single with four bracts. Blooms are normally carried on trusses. Once flowering has been initiated, it continues over a long period.

Blooming Season: The new variety when propagated by leaf cuttings can be flowered any season of the year by applying recognized greenhouse procedures for manipulating day length and temperatures. Traditional propagating and growing practices would allow for natural flowering in late November and early December in northern latitudes.

Foliage: Alternate; borne at close angle to the stems; persistant; heavy; glossy; some twisting at maturity; leathery texture:

*Size.*—Medium to large approximately 10 to 12 centimeters long and 8 to 10 centimeters wide. Environmental and general plant conditions can greatly alter the size and color of the foliage.

*Shape.*—Generally oval, pointed, heart shaped.

*Texture.*—Upper side—leathery, glossy; under side—smooth, highly reflective.

*Margin.*—Slightly serrated, some twisting.

*Color.*—Mature leaves: Upper side—between 147A and 137A; under side—147B–C. Young leaves: Upper side—137A–B red margins; under side—138B.

Disease Resistance: The foliage is quite resistant to common powdery mildew when tested under normal glasshouse conditions in comparison to cultivars introduced prior to the development of the Rieger begonias.

Flowers:

*Borne.*—On trusses with several to a stem in regular clusters. Individual blooms have above average keeping qualities and maintain a bright pink color under varying conditions. Normally four petals per bloom. The diameter of the bloom regularly measures 6 to 7 centimeters in diameter. Flowers are male with a yellow center of stamens and anthers.

*Quantity.*—Bloom quantity is somewhat less than the parent variety, but is offset by larger individual blooms. Flowering is continuous over a relatively long period of time.

*Flower Buds.*—Develop progressively at the terminal nodes to the size of flat coin upwards to two centimeters in diameter. A lighter shade of pink is prevalent on the back side of the petals at this time.

*Petals.*—Red 48 B–C.

*Reproductive Organs.*—Stamens quite abundant. Color 14 A–B. Styles/ovaries—none seen to date.

I claim:

1. A new and distinct variety of elatior begonia characterized particularly by its clear blue-pink color of the large flower petals, compact and sturdy plant growth, its capability of being propagated from leaf cuttings that allows for sufficient controls to permit planned commercial flowering at any time of the year, greater resistance to common powdery mildew, dark green heavy crisp foliage distinguished by some twisting at maturity, and by its improved appearance and durability compared to the parent variety Riegers Schwabenland Pink.

No references cited.

ROBERT E. BAGWILL, Primary Examiner